US006541432B2

(12) United States Patent
Kaneda et al.

(10) Patent No.: US 6,541,432 B2
(45) Date of Patent: Apr. 1, 2003

(54) CLEANSING MATERIAL

(75) Inventors: Kenji Kaneda, Tokyo (JP); Keiko Matsuo, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/838,270

(22) Filed: Apr. 20, 2001

(65) Prior Publication Data

US 2001/0046948 A1 Nov. 29, 2001

(30) Foreign Application Priority Data

Apr. 21, 2000 (JP) ........................................ 2000-121705

(51) Int. Cl.[7] .................................................. A61K 7/50
(52) U.S. Cl. ........................ 510/136; 510/137; 510/157; 510/438; 424/401; 424/443
(58) Field of Search ................................ 510/136, 137, 510/157, 155, 438, 439; 424/401, 443

(56) References Cited

U.S. PATENT DOCUMENTS 5,908,707 A * 6/1999 Cabell et al. ............. 428/537.5
5,980,924 A    11/1999 Yamazaki et al.
6,197,315 B1 * 3/2001 Beerse et al.

FOREIGN PATENT DOCUMENTS

| EP | 0 870 496 A2 | 10/1998 |
|---|---|---|
| JP | 59-20400 | 2/1984 |
| JP | 05-156300 | 6/1993 |
| JP | 05-163116 | 6/1993 |
| JP | 07-223922 | 8/1995 |
| JP | 8-40826 | 2/1996 |
| JP | 08-040826 | 2/1996 |
| JP | 08-092031 | 4/1996 |
| JP | 08-165220 | 6/1996 |
| JP | 08-198733 | 8/1996 |
| JP | 10-251118 | 9/1998 |
| JP | 11-021211 | 1/1999 |
| JP | 11-49641 | 2/1999 |
| JP | 11-286081 | 10/1999 |

* cited by examiner

Primary Examiner—Necholus Ogden
(74) Attorney, Agent, or Firm—Oblon, Spivak, McClelland, Maier & Neustadt, P.C.

(57) ABSTRACT

A cleansing material comprising a sheet material impregnated with an emulsion having a viscosity of 200 to 4000 mPa·s at 25° C. and a viscosity of 100 to 2000 mPa·s at 50° C.

17 Claims, No Drawings

CLEANSING MATERIAL

FIELD OF THE INVENTION

This invention relates to a cleansing material which exerts an excellent cleansing effect on various makeup stains, and which sufficiently removes both aqueous makeup cosmetics and oily makeup cosmetics conveniently, quickly and sufficiently.

BACKGROUND OF THE INVENTION

Makeup cosmetics must be highly adhesive to the skin, and highly resistant to moisture and sebum, so that they do not easily come off but, instead, last longer. In particular, mascara, which is one type of makeup cosmetics, contains solid waxes (beeswax, etc.), film-forming resins (acrylic resins, etc.) or emulsions thereof to give oily (water-proof) mascara products. Alternatively, makeup cosmetics may use water-soluble resins capable of forming film (polyvinyl alcohol, etc.) to give aqueous mascara products, thereby providing products which do not easily come off, but which last longer.

On the other hand, it is also necessary to efficiently remove makeup cosmetics and, thus, various cleansing materials have been employed therefore, for example: cleansing oils containing oily materials as the major components; high-viscosity cleansing compositions (for example, cleansing creams, cleansing gels) consisting essentially of oily components, water and surfactants; and low-viscosity cleansing compositions (for example, cleansing milks and milky lotions).

However, the cleansing oils and the low-viscosity cleansing compositions are inconvenient to use, since it is feared that these products would drip and stain, for example, clothes or washstands. On the other hand, high-viscosity cleansing compositions tend to take a very long time to exert the cleansing effect. Furthermore, these cleansing compositions are designed to remove either oily makeup cosmetics (for example, oily (water-proof) mascara), or to remove aqueous makeup cosmetics (for example, aqueous mascara), but cannot remove both types of makeup cosmetics at the same time.

There have been proposed two-phase cleansing compositions—containing an oily phase and an aqueous phase separated from each other—which aim at removing both of oily (water-proof) mascara and aqueous mascara at the same time. The waterproof mascara is removed by the oily phase of such cleansing compositions and the aqueous mascara is removed by the aqueous phase. However, these products are inconvenient to use, since they must be vigorously shaken by hand to give an apparently homogeneous dispersion before use, then must be absorbed by a cotton absorbent or a tissue sheet, followed by wiping the makeup cosmetics from the skin. Moreover, it is difficult to control the optimum amount of such products.

Accordingly, there have been proposed cleansing materials packed individually wherein a sheet material, which is made of a non-woven fabric or cotton, is impregnated with such a two-phase cleansing composition (see, for example, JP-A-8-40826, claim 1: the term "JP-A" as used herein means an "unexamined published Japanese patent application").

In case of the cleansing composition described in JP-A-8-40826, the oily phase and the aqueous phase of the two-phase cleansing composition are liable to separate from each other within the sheet material. As a result, the cleansing performance varies in the upper part and the lower part of the sheet material, or on the front face and the back face thereof. Therefore, the cleansing effect is worsened.

To solve this problem, there also have been proposed sheet-type cleansing materials comprising a sheet material, which is made of, for example, cotton or a non-woven fabric impregnated with an aqueous cleansing composition containing an aqueous solution of a surfactant (see, for example, JP-A-11-49641). These cleansing materials have excellent handling properties and are convenient to use, but are insufficient for removing oily (water-proof) mascara.

SUMMARY OF THE INVENTION

An object of the present invention is to provide cleansing materials which exert an excellent cleansing effect on various makeup stains, and which remove both of aqueous makeup cosmetics and oily makeup cosmetics sufficiently, conveniently and quickly.

The inventors have found that an emulsion cosmetic (herein after "emulsion") having a viscosity within a specific range is excellent in stability per se (liquid stability), and shows a high storage stability (impregnated sheet stability), without undergoing phase separation over a long period of time when employed in a cleansing material prepared by impregnating a sheet material therewith. The inventors have further found that such an emulsion exerts a high cleansing efficacy on makeup cosmetics (in particular, both of oily (water-proof) mascara and aqueous mascara) and has excellent handling properties.

Accordingly, the invention relates to a cleansing material comprising a sheet material impregnated with an emulsion having a viscosity of 200 to 4000 mPa·s at 25° C. and a viscosity of 100 to 2000 mPa·s at 50° C.

DETAILED DESCRIPTION OF THE INVENTION

The cleansing material according to the invention comprises a sheet material impregnated with an emulsion.

The "emulsion" as used herein, is in the state where oily components and aqueous components have been homogeneously emulsified. Owing to the above-described characteristics, a cleansing material according to the invention is capable of removing not only oily makeup cosmetics (for example, oily mascara), but also aqueous makeup cosmetics (for example, aqueous mascara) at the same time. The emulsion used herein may be either one of the W/O type or the O/W type. The cleansing material according to the present invention has excellent handling properties, and is convenient to use.

The emulsion used in the present invention has a viscosity of 200 to 4000 mPa·s (preferably 500 to 3000 mPa·s) at 25° C. and a viscosity of 100 to 2000 mPa·s (preferably 100 to 1200 mPa·s) at 50° C. When the viscosity at 25° C. or 50° C. is lower than the level as defined above (i.e., an emulsion of relatively low viscosity), it is impossible to ensure any sufficient liquid stability of the emulsion. When the viscosity exceeds the level as defined above (i.e., an emulsion of relatively high viscosity), the emulsion fails to sufficiently remove makeup cosmetics and fails to impregnate into the sheet material.

The emulsion useful herein contains at least an oily component, water, and a surfactant.

When the concentration of the oily component in the emulsion is too small, it is impossible to achieve any sufficient cleansing effect on oily makeup cosmetics. On the other hand, when the concentration of the oily component is too large, the user's skin texture tends to become oily after wiping. It is therefore preferable that the concentration of the oily component ranges from 10 to 80% by weight, and more preferably from 20 to 70% by weight.

The oily component used in the emulsion of the present invention may include those commonly employed as cosmetic materials. It is possible to use two or more oily components in combination. Examples of the oily component include: hydrocarbons, such as liquid paraffin and squalane; higher alcohols, such as stearyl alcohol, cetyl alcohol and oleyl alcohol; fatty acids, such as oleic acid and linoleic acid; dialkyl ethers, such as isostearyl octyl ether, cetyl-1-methylpropyl ether and cetyl-1,3-dimethylbutyl ether; fatty acid esters, such as isopropyl myristate and isopropyl palmitate; fatty acid triglycerides; and silicones, such as cyclic silicones and chain-type dimethylpolysiloxane with a low degree of polymerization.

When the water content in the emulsion is too small, it is impossible to achieve any sufficient cleansing effect on aqueous makeup cosmetics. On the other hand, when the content of water is too large, it is impossible to obtain any sufficient cleansing effect on oily makeup cosmetics. It is therefore preferable that the content of water ranges from 10 to 80% by weight, still preferably from 20 to 70% by weight.

When the concentration of the surfactant in the emulsion is too small, the emulsion shows an insufficient stability in the sheet material. On the other hand, when the content of the surfactant is too large, the user's skin texture becomes sticky after wiping. It is therefore preferable that the content of the surfactant ranges from 0.5 to 10% by weight, still preferably from 0.5 to 5% by weight.

The surfactant useful herein may include those commonly employed as cosmetic materials. Also, it is possible to use two or more surfactants in combination. Examples of the surfactant include: nonionic surfactants (for example, polyoxyethylene alkyl ethers, sucrose fatty acid esters, fatty acid monoglycerides, sorbitan fatty acid esters optionally having polyoxyalkylenes added thereto, polyoxyethylene hardened castor oil and fatty acid esters thereof, polyoxyalkylene fatty acid esters); anionic surfactants (for example, sulfate-type surfactants such as alkylsulfuric acid salts, polyoxyethylene alkylsulfuric acid salts, sulfosuccinic acid-type surfactants, taurate-typesurfactants, isethionate-type surfactants and α-olefinsulfonate-type surfactants, sulfonate-type surfactants, carboxylate-type surfactants such as fatty acid soaps, ether carboxylic acid-type surfactants and acylated amino acid-type surfactants, and phosphate-type surfactants such as alkylphosphoric acid ester-type surfactants); and amphoteric surfactants (for example, carbobetaine-type surfactants, phosphobetaine-type surfactants, sulfobetaine-type surfactants, imidazoliniumbetaine-type surfactants).

The emulsion may further contain at least one thickening agent selected from the group consisting of aqueous thickening agents and oily thickening agents so as to control the viscosity, if necessary.

Examples of the aqueous thickening agents useful herein include carrageenan, xanthan gum, starch, guar gum, gum alabic, locust bean gum, glucomannan, pectin, gelatin, carboxymethylcellulose or its salt, methylcellulose, hydroxethylcellulose, polyvinyl alcohol, polyvinyl pyrrolidone, carboxyvinyl polymer, and sodium polyacrylate.

Examples of the oily thickening agents include high-molecular weight substances and waxes (for example, carnauba wax, beeswax, polyethylene, paraffin, wax, Japan wax); metal soaps (for example, magnesium stearate, aluminum stearate); inorganic gelling agents (for example, anhydrous silicic acid, lipophilic bentonite); organic gelling agents (for example, polyamides, amino acid derivatives, dextrin higher fatty acid esters, lipophilic sucrose fatty acid esters); and metal dialkylphosphates.

The emulsion may further contain various additives commonly employed in cosmetics (for example, solvents, humectants), if necessary.

In the present invention, the sheet material to be impregnated with the emulsion can be any one of the well-known sheet materials having a favorable skin texture for cleansing. For example, the sheet material used herein may include non-woven fabrics (for example, non-woven cellulose fabric, non-woven rayon fabric, non-woven polyester acetate fabric) and natural cotton sheets. The non-woven fabric preferably, from the viewpoint of obtaining a favorable skin texture, is obtained by the water-entangling method, or may be obtained by combining two or more fibers or a sheet material prepared by laminating or bonding two or more sheets. Particularly, it is preferable to use a sheet material that can be quickly impregnated with the emulsion (which has a viscosity of 200 to 4000 mPa·s at 25° C. and which has a viscosity of 100 to 2000 mPa·s at 50° C.), and that can allow the impregnating emulsion to be stable thereon.

Examples of the sheet materials obtained by combining two or more fiber materials include non-woven fabrics obtained by combining cellulose fibers (including cellulose and rayon) with polyester fibers—including PET (polyethylene terephthalate), and PBT (polybutylene terephthalate). From the viewpoint of achieving a favorable skin texture and an appropriate elasticity, preferably the ratio of cellulose fiber/polyester fiber is the range of from 50/50 to 90/10.

To maintain the emulsion in a favorable state, it is preferable that the sheet material to be used in the invention has a cellulose content (determined by the NMR method) of at least 30% by weight, still preferably at least 50% by weight.

When an average basis weight (weight per unit area) of the sheet material is too small, shape retention of the sheet material deteriorates. On the other hand, when the average basis weight is too large, the sheet material is inflexible and its handling property deteriorates. It is therefore preferable that the average basis weight of the sheet material is from 20 to 120 g/m$^2$, still preferably from 30 to 100 g/m$^2$.

To adequately scratch off stains and keep a favorable skin texture, it is preferable that the average fineness of the fibers is 5 d (denier) or less, still preferably 3 d or less (as denier is determined under an electron microscope).

From the viewpoints of favorable skin texture, adequate performance of scratching off stains, and shape retention, it is preferable that the dry reflectivity of the sheet material, which indicates the fiber density, is at least 45%. The reflectivity can be determined by measuring it a plurality of times (for example, 5 to 10 times) with the use of a color difference meter of the spectroscopic curve/reflectivity mode (SZ-Σ80 manufactured by Nippon Denshoku K.K., wherein the measurement conditions are: lens diameter: 30 mm, sample stand, light source: C/2, measurement wavelength: 500 nm) and then calculating the average.

The sheet material useful herein has a suitable shape, size, and thickness, from the standpoint of handling properties. For example, the sheet material is preferably in a square, rectangular, circular, or oval, shape with a side or diameter of about 5 to 10 cm and a thickness of about 0.2 to 4 mm.

The sheet material preferably is impregnated with the emulsion at a ratio of from 1 to 10 g, and still more preferably from 2 to 5 g, per gram of the sheet material.

The cleansing material according to the invention can be produced by applying the emulsion to the sheet material by dropping the emulsion from a nozzle, or by spraying it, and then allowing the sheet to stand so as to allow the emulsion to sufficiently impregnate into the sheet material.

Typically, the cleansing material according to the invention is packed in one or more sheets into a bag and then sealed. Before using, the bag is opened and the sheet-type cleansing material is taken out. Then, the sheet-type cleansing material is pressed onto the skin from which makeup cosmetics are to be removed so that the makeup cosmetics are wiped off irrespective of the cosmetics' nature, i.e., either oily makeup cosmetics or aqueous ones. Thus, the cleansing material can achieve an excellent cleansing effect on various cosmetic stains. Also, both of aqueous makeup cosmetics and oily makeup cosmetics can be sufficiently removed conveniently and quickly.

Even after storing over a long time, the cleansing material according to the invention shows no separation of the emulsion impregnated into the sheet material. Namely, it is excellent in storage stability. In particular, when the cleansing material is stored at 50° C. for 1 month, the emulsion substantially undergoes no separation. The term "substantially undergoing no separation" as used herein means that the difference in moisture contents is less than 30% when the stability of the impregnated sheet of cleansing material is evaluated under the conditions as will be described in Examples hereinafter.

EXAMPLES

Now, the invention will be described in greater detail by reference to the following Examples.

Examples 1 to 4 and Comparative Examples 1 and 2

Emulsion for cleansing (W/O type emulsions) as specified in Table 1 were prepared by a conventional method and the viscosities were measured. Also, the liquid stability of each emulsion per se was evaluated.

Subsequently, a sheet material (non-woven fabric made of rayon/PET=70/30, basis weight: 70 g/m², size 5×10 cm, fineness: 1.5 d) was impregnated with 1.2 g of each W/O emulsion, prepared as above. Thus, sheet-type cleansing materials of Examples 1 to 4 and Comparative Examples 1 and 2 were produced.

Each of the cleansing materials of Examples 1 to 4 and Comparative Examples 1 and 2 thus produced were (by the method as will be illustrated hereinbelow) tested and evaluated in: (i) the ease in impregnation of the W/O emulsion into the sheet material (i.e., impregnation properties); (ii) the stability of the impregnated sheet of cleansing material; (iii) the cleansing effect on aqueous mascara employed as an aqueous makeup cosmetics, and the cleansing effect on oily mascara employed as an oily makeup cosmetics; (iv) the handling properties and the convenience in use; and (v) the skin texture after wiping. Table 2 summarizes the obtained results.

(Viscosity)

About 100 g of a W/O emulsion was introduced into a wide mouthed glass bottle (120 ml) and the whole bottle, excluding the cap, was immersed in a water bath maintained at a constant temperature (25° C. or 50° C.) for 2 hours. After 2 hours, the glass bottle was immediately taken up from the water bath and set to a Brookfield type viscometer (Model BM, manufactured by Tokyo Keiki K.K.) provided with a No. 3 rotor. Then, the viscosity was measured at 30 r.p.m. for 1 minute. The value thus indicated was multiplied by the number (40) specified under the measurement conditions to thereby determine the viscosity (mPa·s) at the measurement temperatures.

(Liquid Stability)

Immediately after the completion of the preparation, a W/O emulsion was packed into a glass tube (having an inner diameter of about 23 mm) to give a liquid height of 40 mm. The tube was then capped and stored in a preserver at 50° C. for 1 month. Subsequently, the tube was taken out from the preserver and cooled down to room temperature. At this point, the thickness of the separated layer, if any, of the W/O emulsion in the upper or lower part of the glass tube was measured with a ruler, and evaluation was made on the basis of the following criteria.

Rank Standard

A: Showing no separation.

B: Showing a separated layer of 1 to 3 mm in thickness.

C: Showing a separated layer of 4 mm or more in thickness (Stability of Impregnated Sheet)

A sheet-type cleansing material (5 cm×10 cm) was folded in two to give a piece of 5 cm×5 cm. Ten folded pieces were piled up on each other and then weighed. Next, the pieces were put into an aluminum pillow (9 cm×12 cm) and sealed. Then, the pillow was stored at 50° C. and so that the cleansing material in the pillow was located perpendicular to the floor. After storing for 1 month, the cleansing material was taken out from the aluminum pillow and halved with scissors. Next, the upper and lower halves were introduced separately into containers with a lid and weighed (this weight is variable "A" as used below).

Separately, dry ethanol (moisture content: 0.1% or less) was prepared by adding an appropriate amount of molecular sieves (manufactured by Wako Pure Chemical Industries, Ltd.) to reagent-grade ethanol (99.5%, manufactured by Katayama Kagaku Kogyo K.K.). About 8 g (this is variable "B" as used below) portions of this dry ethanol was precisely weighed and poured into respective containers. The containers, each containing the cleansing material pieces as halved above and the dry ethanol, were stirred with a touch mixer (Model MT-31, manufactured by Yamato Kagaku) for 1 minute and then subjected to ultrasonication with an ultrasonic washing machine (US-1, manufactured by SND K.K.) for 20 minutes at 40° C. After that, each mixture was cooled down to room temperature. A portion of about 100 µl thereof was weighed with a microsyringe (MS-N100) and the water content (this is variable "C", in percent, as used below) was measured with a water content meter (Model AQ-6, manufactured by Hiranuma Sangyo K.K.) in which the sample weight had been input. After the completion of the measurement, the cleansing material was taken out from the container, washed and sufficiently dried at room temperature. Then the dried cleansing material was weighed (this weight is variable "D" as used below). The water content (in percent) was then calculated in accordance with the following formula 1.

Water content (%)=$(Cx((A-D)+B)/100)\div(A-D)\times100$. (Formula 1)

By using the difference in water content (%) between the upper and lower halves of the sheets as an indication, the impregnated sheets of the cleansing materials were evaluated in stability in accordance with the following criteria.

Rank Standard
A: Difference in moisture contents <10%.
B: 10% ≦Difference in moisture contents <30%.
C: Difference in moisture contents >30%.

(Impregnation Properties)

A sheet material (5 cm×10 cm) was impregnated with 1.1 g of an emulsion, and the ease in impregnation was evaluated in accordance with the following criteria.

Rank Standard
A: Easily impregnates.
B: Moderately impregnates.
C: Hardly impregnates.

(Cleansing Performance)

A mascara Deffinicil Noir Infini (manufactured by Lancôme) as an aqueous makeup cosmetics, and another mascara Maybelline Dial Mascara Black (manufactured by Maybelline Co.) as an oily makeup cosmetics, were prepared. Each mascara (about 20 mg) was applied on a slide glass plate to form a circle of about 2 cm in radius and dried by allowing to stand over day and night.

Next, a slide glass plate on which no mascara had been applied was placed on a white paper sheet, and the chromaticity ($E_0$) was determined with a color difference meter (CR-300, manufactured by Minolta Camera Co., Ltd.). Subsequently, the slide glass plate, on which the mascara had been applied, was placed on the white paper sheet and the mascara stain before cleansing was measured to determine the chromaticity ($E_1$). Then, each of the cleansing materials (Examples 1 to 4, Comparative Examples 1 and 2) was placed on the mascara stain and lightly pressed thereon for 5 seconds. Next, the mascara stain was wiped off 10 times using the same cleansing material, and then the chromaticity ($E_2$) was determined again. Subsequently, the cleansing ratio (%) was calculated in accordance with the following formula 2. A cleansing ratio close to 100 indicates a favorable cleansing performance level, i.e., as cleansing ratios increase towards 100, the cleansing performance level increases as well.

Cleansing ratio (%)=$(1-(E_0-E_2)/(E_0-E_1))\times100$. (Formula 2)

(Handling Properties and Convenience)

Five skilled panelists applied the aqueous mascara and oily mascara, as employed in the evaluation of the cleansing performance, to respective eyelashes. After drying for 6 hours, the makeup cosmetics were removed by the methods respectively appropriate for the makeup cosmetics. The handling properties and convenience were then evaluated in accordance with the following criteria. The average of the scores given by the five panelists was determined.

| Standard | Score |
| --- | --- |
| Good: | 5 |
| Somewhat good: | 4 |
| Moderate: | 3 |
| Somewhat poor: | 2 |
| Poor | 1. |

(Skin Texture)

Five skilled panelists applied the aqueous mascara and oily mascara, as employed in the evaluation of the cleansing performance, to respective eyelashes. After drying for 6 hours, the makeup cosmetics were removed by each sheet-type cleansing material. The skin texture was then evaluated in accordance with the following criteria. The average of the scores given by the five panelists was determined.

| Standard | Score |
| --- | --- |
| Not sticky: | 3 |
| Somewhat sticky: | 2 |
| Sticky: | 1. |

TABLE 1

| Component (wt. %) | Ex. 1 | Ex. 2 | Ex. 3 | Ex. 4 | Comp. Ex. 1 | Comp. Ex. 2 |
| --- | --- | --- | --- | --- | --- | --- |
| Liquid paraffin | 30.0 | 30.0 | 30.0 | 25.0 | — | 30.0 |
| Methyl cyclopolysiloxane | 10.0 | 10.0 | — | 20.0 | 50.0 | 10.0 |
| Cetyl-1,3-dimethylbutyl ether | 10.0 | 10.0 | 20.0 | — | — | 10.0 |
| Polyoxyethylene sorbitan monostearate (20 E.O.) | 2.0 | 2.0 | 1.0 | 2.0 | 2.0 | 2.0 |
| Isostearyl glyceryl ether | 0.5 | — | 0.8 | 1.5 | 1.0 | 1.0 |
| Glycerin | 5.0 | 5.0 | 2.0 | 5.0 | 2.0 | 5.0 |
| Xanthan gum | 0.5 | 0.5 | 0.2 | — | — | 1.0 |
| Dextrin palmitate | 3.0 | 3.0 | 2.5 | 2.5 | — | 5.0 |
| Aluminum dialkylphosphate | 1.0 | 1.5 | 1.5 | 1.5 | — | 4.0 |
| Methyl paraben | 0.1 | 0.1 | 0.1 | 0.1 | 0.1 | 0.1 |
| Propyl paraben | 0.1 | 0.1 | 0.1 | 0.1 | 0.1 | 0.1 |
| Purified water | the balance | the balance | the balance | the balance | the balance | the balance |
| Total | 100.0 | 100.0 | 100.0 | 100.0 | 100.0 | 100.0 |

TABLE 2

| Evaluation item | Ex. 1 | Ex. 2 | Ex. 3 | Ex. 4 | Comp. Ex. 1 | Comp. Ex. 2 |
|---|---|---|---|---|---|---|
| Viscosity (mPa·s) | | | | | | |
| 25° C. | 1500 | 1400 | 1200 | 1100 | 150 | 6300 |
| 50° C. | 600 | 550 | 480 | 360 | 80 | 2250 |
| Liquid stability | A | A | A | A | C | A |
| Impregnation properties | A | A | A | A | A | C |
| Impregnated sheet stability | A | A | A | A | C | A |
| Cleansing performance | | | | | | |
| Aqueous mascara | 98 | 98 | 95 | 96 | 96 | 90 |
| Oily mascara | 97 | 97 | 95 | 92 | 94 | 53 |
| Handling properties | 4.8 | 4.8 | 4.8 | 4.6 | 4.6 | 4.6 |
| Convenience | 4.8 | 4.6 | 4.8 | 4.8 | 4.6 | 3.2 |
| Skin texture | 2.6 | 2.6 | 2.6 | 2.8 | 2.8 | 1.8 |

As Table 2 shows, the sheet-type cleansing materials of Examples 1 to 4 achieved favorable results in all of the evaluation items. In particular, these products showed good cleansing performances on both of the aqueous mascara and the oily mascara.

On the other hand, when the emulsion impregnated into the sheet material had a viscosity lower than 200 mPa·s at 25° C., the liquid stability of the emulsion per se became insufficient, and the sheet-type cleansing material prepared by impregnating the sheet material with that emulsion also showed an insufficient stability. Further, when the emulsion impregnated into the sheet material had a viscosity exceeding 4000 mPa·s at 25° C., the sheet material could hardly be impregnated with the emulsion.

That is to say, the cleansing material according to the invention, prepared by impregnating a sheet material with an emulsion having a viscosity within a specific range, exerts an excellent cleansing effect on makeup stains of any type and enables the removal of makeup cosmetics irrespective of nature—i.e., either oily ones or aqueous ones—while achieving favorable handling properties and convenience.

While the invention has been described in detail and with reference to specific examples thereof, it will be apparent to one skilled in the art that various changes and modifications can be made therein without departing from the spirit and scope thereof.

The entire disclosure of each and every foreign patent application from which the benefit of foreign priority has been claimed in the present application is incorporated herein by reference, as if fully set forth herein.

What is claimed is:

1. A cleansing material comprising a sheet material impregnated with an emulsion that has a viscosity of 200 to 4000 mPa·s at 25° C. and a viscosity of 100 to 2000 mPa·s at 50° C.

2. The cleansing material according to claim 1, wherein said sheet material has a cellulose content of at least 30% by weight, has an average basis weight of 20 to 120 g/m², and is made of fibers having an average fineness of 5 d or less.

3. The cleansing material according to claim 1, wherein said emulsion comprises 10 to 80% by weight of an oily component, 10 to 80% by weight of water, and 0.5 to 10% by weight of a surfactant.

4. The cleansing material according to claim 1, further comprising at least one thickening agent selected from the group consisting of an aqueous thickening agent and an oily thickening agent.

5. The cleansing material of claim 1, wherein said emulsion is a water-in-oil type.

6. The cleansing material of claim 1, wherein said emulsion is an oil-in-water type.

7. The cleansing material of claim 1, wherein said emulsion has a viscosity of 500 to 3,000 mPa·s at 25° C.

8. The cleansing material of claim 1, wherein said emulsion has a viscosity of 100 to 1,200 mPa·s at 50° C.

9. The cleansing material of claim 1, wherein said emulsion comprises an oily component, water and a surfactant.

10. The cleansing material of claim 9, wherein said oily component is present in an amount of 10 to 80% by weight.

11. The cleansing material of claim 9, wherein said oily component is selected from the group consisting of a hydrocarbon, a higher alcohol, a fatty acid, a dialkyl ether, a fatty acid ester, a fatty acid triglyceride, a silicone and a mixture thereof.

12. The cleansing material of claim 9, wherein said water is present in an amount of 10 to 80% by weight.

13. The cleansing material of claim 9, wherein said surfactant is present in a range of 0.5 to 10% by weight.

14. The cleansing material of claim 9, wherein said surfactant is selected from the group consisting of a nonionic surfactant, an anionic surfactant, an amphoteric surfactant and a mixture thereof.

15. The cleansing material of claim 4, wherein said aqueous thickening agent is selected from the group consisting of carageenan, xanthan gum, starch, guar gum, gum arabic, locust bean gum, glucomannan, pectin, gelatin, carboxymethycellulose, a salt of carboxymethylcellulose, methylcellulose, hydroxyethylcellulose, polyvinyl alcohol, polyvinyl pyrrolidone, carboxyvinylpolymer, sodium polyacrylate and a mixture thereof.

16. The cleansing material of claim 4, wherein said oily thickening agent is selected from the group consisting of a high-molecular weight substance, a wax, a metal soap, an inorganic gelling agent, an organic gelling agent, a metal dialkyiphosphate and mixtures thereof.

17. A method for removing makeup comprising wiping a surface of skin comprising a makeup selected from the group consisting of an aqueous makeup, an oily makeup or a mixture thereof, with the cleansing material of claim 1.

* * * * *